United States Patent
Talish et al.

(10) Patent No.: US 7,211,060 B1
(45) Date of Patent: May 1, 2007

(54) ULTRASOUND BANDAGES

(75) Inventors: Roger J. Talish, Hillsborough, NJ (US); Alan A. Winder, Westport, CT (US)

(73) Assignee: Exogen, Inc., Piscataway, NJ (US)

( * ) Notice: Subject to any disclaimer, the term of this patent is extended or adjusted under 35 U.S.C. 154(b) by 0 days.

(21) Appl. No.: 09/700,014

(22) PCT Filed: May 6, 1999

(86) PCT No.: PCT/US99/09875

§ 371 (c)(1),
(2), (4) Date: Dec. 29, 2000

(87) PCT Pub. No.: WO99/56829

PCT Pub. Date: Nov. 11, 1999

Related U.S. Application Data (60) Provisional application No. 60/084,453, filed on May 6, 1998.

(51) Int. Cl.
*A61F 5/00* (2006.01)

(52) U.S. Cl. .............. 602/2; 602/1; 602/41; 601/2; 600/407

(58) Field of Classification Search .............. 602/1, 602/2, 41; 601/2; 600/407
See application file for complete search history.

(56) References Cited

U.S. PATENT DOCUMENTS

| | | |
|---|---|---|
| 1,604,870 A | 10/1926 | Asman |
| 3,134,451 A | 5/1964 | Hanssen |
| 3,193,034 A | 7/1965 | Hutchinson et al. |

(Continued)

FOREIGN PATENT DOCUMENTS

AU 199950292 2/2000

(Continued)

OTHER PUBLICATIONS

U.S. Appl. No. 09/040,157, filed Mar. 17, 1998, Talish.

(Continued)

*Primary Examiner*—Henry Bennett
(74) *Attorney, Agent, or Firm*—Bruce D. Gray; Kilpatrick Stockton LLP (57) ABSTRACT

Ultrasound bandages (10) and ultrasound transducer array bandages are provided herein to accelerate the healing of wounds by positioning the ultrasound bandages (10) and ultrasound transducer array bandages adjacent to a wound and generating ultrasonic pulses. The ultrasound bandages (10) generally include (a) a backing layer (12), (b) an adhesive layer (14) applied to, and substantially coextensive with the backing layer (12), and (c) a transducer material (16) disposed on at least a portion of the adhesive layer (14). The ultrasound transducer array bandages generally include (a) a backing layer (13), (b) an adhesive layer applied to, and substantially coextensive with, the backing layer, and (c) an array comprising a plurality of transducer materials arranged in adjacent relation to define spaces therebetween, the array being disposed on at least a portion of the adhesive layer. The resulting ultrasound bandages (10) and ultrasound transducer array bandages allows for medical therapeutic applications as promoting the healing of wounds such as abrasions, lacerations, incisions and ulcers at any section or multiple sections of the human anatomy with the ultrasound bandages (10) and ultrasound transducer array bandages being conveniently discarded after each application and a new bandage then being applied for the next application.

83 Claims, 5 Drawing Sheets

U.S. PATENT DOCUMENTS

| | | |
|---|---|---|
| 3,304,036 A | 2/1967 | Davis |
| 3,310,049 A | 3/1967 | Clynes |
| 3,433,663 A | 3/1969 | Underwood |
| 3,499,437 A | 3/1970 | Balamuth |
| 3,550,586 A | 12/1970 | Balamuth |
| 3,594,993 A | 7/1971 | Heyse |
| 3,701,352 A | 10/1972 | Bosworth |
| 3,760,799 A | 9/1973 | Crowson |
| 3,767,195 A | 10/1973 | Dimick |
| 3,828,769 A | 8/1974 | Mettler |
| 3,855,638 A | 12/1974 | Pilliar |
| 3,961,380 A | 6/1976 | Garr |
| 3,986,212 A | 10/1976 | Sauer |
| 4,037,592 A | 7/1977 | Kronner |
| 4,105,017 A | 8/1978 | Ryaby et al. |
| 4,108,165 A | 8/1978 | Kopp et al. |
| 4,127,125 A | 11/1978 | Takemoto et al. |
| 4,164,794 A | 8/1979 | Spector et al. |
| 4,170,045 A | 10/1979 | Estes |
| 4,176,664 A | 12/1979 | Kalish |
| 4,206,516 A | 6/1980 | Pilliar |
| 4,216,766 A | 8/1980 | Duykers et al. |
| 4,227,111 A | 10/1980 | Cross et al. |
| 4,233,477 A | 11/1980 | Rice et al. |
| 4,269,797 A | 5/1981 | Mikiya et al. |
| 4,296,753 A | 10/1981 | Goudin |
| 4,312,536 A | 1/1982 | Lloyd |
| 4,315,503 A | 2/1982 | Ryaby et al. |
| 4,351,069 A | 9/1982 | Ballintyn et al. |
| 4,355,428 A | 10/1982 | Deloison et al. |
| 4,358,105 A | 11/1982 | Sweeney, Jr. |
| 4,361,154 A | 11/1982 | Pratt, Jr. |
| 4,365,359 A | 12/1982 | Raab |
| 4,383,533 A | 5/1983 | Lovelace et al. |
| 4,421,119 A | 12/1983 | Pratt, Jr. |
| 4,431,038 A | 2/1984 | Rome |
| 4,440,025 A | 4/1984 | Hayakawa et al. |
| 4,441,486 A | 4/1984 | Pounds |
| 4,446,586 A | 5/1984 | Reed et al. |
| 4,452,326 A | 6/1984 | Hanssen et al. |
| 4,476,874 A | 10/1984 | Taenzer et al. |
| 4,511,921 A | 4/1985 | Harlan et al. |
| 4,530,360 A | 7/1985 | Duarte |
| 4,536,894 A | 8/1985 | Galante et al. |
| 4,542,539 A | 9/1985 | Rowe, Jr. et al. |
| 4,542,744 A | 9/1985 | Barnes et al. |
| 4,550,714 A | 11/1985 | Talish et al. |
| 4,556,066 A | 12/1985 | Semrow |
| 4,570,640 A | 2/1986 | Barsa |
| 4,573,996 A | 3/1986 | Kwiatek et al. |
| 4,594,662 A | 6/1986 | Devaney |
| 4,612,160 A | 9/1986 | Donlevy et al. |
| 4,627,429 A | 12/1986 | Tsuk |
| 4,630,323 A | 12/1986 | Sage et al. |
| 4,644,942 A | 2/1987 | Sump |
| 4,669,483 A | 6/1987 | Hepp et al. |
| 4,677,438 A | 6/1987 | Michiguchi et al. |
| 4,687,195 A | 8/1987 | Potts |
| 4,708,127 A | 11/1987 | Abdelghani |
| 4,710,655 A | 12/1987 | Masaki |
| 4,725,272 A * | 2/1988 | Gale .................. 424/448 |
| 4,726,099 A | 2/1988 | Card |
| 4,763,661 A | 8/1988 | Sommer et al. |
| 4,770,184 A | 9/1988 | Greene, Jr. et al. |
| 4,774,959 A | 10/1988 | Palmer et al. |
| RE32,782 E | 11/1988 | Pratt, Jr. |
| 4,782,822 A | 11/1988 | Ricken |
| 4,787,070 A | 11/1988 | Suzuki et al. |
| 4,787,888 A | 11/1988 | Fox |
| 4,792,336 A | 12/1988 | Hlavacek et al. |
| 4,802,477 A | 2/1989 | Gabbay |
| 4,830,015 A | 5/1989 | Okazaki |
| 4,836,316 A | 6/1989 | Carnevale et al. |
| 4,855,911 A | 8/1989 | Lele et al. |
| 4,858,599 A | 8/1989 | Halpern |
| 4,867,169 A | 9/1989 | Machida et al. |
| 4,891,849 A | 1/1990 | Robinson |
| 4,905,671 A | 3/1990 | Senge et al. |
| 4,913,157 A | 4/1990 | Pratt, Jr. et al. |
| 4,917,092 A | 4/1990 | Todd et al. |
| 4,926,870 A | 5/1990 | Brandenburger |
| 4,932,951 A | 6/1990 | Liboff et al. |
| 4,933,230 A | 6/1990 | Card et al. |
| 4,936,303 A | 6/1990 | Detwiler et al. |
| 4,941,474 A | 7/1990 | Pratt, Jr. |
| 4,947,853 A | 8/1990 | Hon |
| 4,979,501 A | 12/1990 | Valchanov et al. |
| 4,982,730 A | 1/1991 | Lewis, Jr. |
| 4,986,275 A | 1/1991 | Ishida et al. |
| 4,993,413 A | 2/1991 | McLeod et al. |
| 4,995,883 A | 2/1991 | Demane et al. |
| 5,000,183 A | 3/1991 | Bonnefous |
| 5,000,442 A | 3/1991 | Dalebout et al. |
| 5,003,965 A | 4/1991 | Talish et al. |
| 5,004,476 A | 4/1991 | Cook |
| 5,016,641 A | 5/1991 | Schwartz |
| 5,018,285 A | 5/1991 | Zolman et al. |
| 5,046,484 A | 9/1991 | Bassett et al. |
| 5,054,490 A | 10/1991 | Rossman et al. |
| 5,067,940 A | 11/1991 | Liboff et al. |
| 5,080,672 A | 1/1992 | Bellis |
| 5,088,976 A | 2/1992 | Liboff et al. |
| 5,099,702 A | 3/1992 | French |
| 5,100,373 A | 3/1992 | Liboff et al. |
| 5,103,806 A | 4/1992 | McLeod et al. |
| 5,106,361 A | 4/1992 | Liboff et al. |
| 5,107,853 A | 4/1992 | Plyter |
| 5,108,452 A | 4/1992 | Fallin |
| 5,133,420 A | 7/1992 | Smith |
| 5,134,999 A | 8/1992 | Osipov |
| 5,139,498 A | 8/1992 | Astudillo Ley |
| 5,140,988 A | 8/1992 | Stouffer et al. |
| 5,143,069 A | 9/1992 | Kwon et al. |
| 5,143,073 A | 9/1992 | Dory |
| 5,163,598 A | 11/1992 | Peters et al. |
| 5,172,692 A | 12/1992 | Kulow et al. |
| 5,178,134 A | 1/1993 | Vago |
| 5,181,512 A | 1/1993 | Viebach et al. |
| 5,184,605 A | 2/1993 | Grzeszykowski |
| 5,186,162 A | 2/1993 | Talish et al. |
| 5,191,880 A | 3/1993 | McLeod et al. |
| 5,197,475 A | 3/1993 | Antich et al. |
| 5,201,766 A | 4/1993 | Georgette |
| 5,209,221 A | 5/1993 | Riedlinger |
| 5,211,160 A | 5/1993 | Talish et al. |
| 5,230,334 A | 7/1993 | Klopotek |
| 5,230,345 A | 7/1993 | Curran et al. |
| 5,230,921 A | 7/1993 | Waltonen et al. |
| 5,235,981 A | 8/1993 | Hascoet et al. |
| 5,254,123 A | 10/1993 | Bushey |
| 5,259,384 A | 11/1993 | Kaufman et al. |
| 5,269,306 A | 12/1993 | Warnking et al. |
| 5,273,028 A | 12/1993 | McLeod et al. |
| 5,284,143 A | 2/1994 | Rattner |
| 5,285,788 A | 2/1994 | Arenson et al. |
| 5,295,931 A | 3/1994 | Dreibelbis et al. |
| 5,301,683 A | 4/1994 | Durkan |
| 5,307,284 A | 4/1994 | Brunfeldt et al. |
| 5,309,898 A | 5/1994 | Kaufman et al. |
| 5,310,408 A | 5/1994 | Schryver et al. |
| 5,314,401 A | 5/1994 | Tepper |
| 5,316,000 A | 5/1994 | Chapelon et al. |
| 5,318,561 A | 6/1994 | McLeod et al. |
| 5,318,779 A | 6/1994 | Hakamatsuka et al. |

| | | | | | | |
|---|---|---|---|---|---|---|
| 5,322,067 A | 6/1994 | Prater et al. | | 5,779,600 A | 7/1998 | Pape |
| 5,323,769 A | 6/1994 | Bommannan et al. | | 5,785,656 A | 7/1998 | Chiabrera et al. |
| 5,327,890 A | 7/1994 | Matura et al. | | 5,818,149 A | 10/1998 | Safari et al. |
| 5,330,481 A | 7/1994 | Hood et al. | | 5,829,437 A | 11/1998 | Bridges |
| 5,330,489 A | 7/1994 | Green et al. | | 5,868,649 A | 2/1999 | Erickson et al. |
| 5,334,214 A | 8/1994 | Putnam | | 5,871,446 A | 2/1999 | Wilk |
| 5,339,804 A | 8/1994 | Kemp | | 5,886,302 A | 3/1999 | Germanton et al. |
| 5,340,510 A | 8/1994 | Bowen | | 5,891,143 A | 4/1999 | Taylor et al. |
| 5,351,389 A | 10/1994 | Erickson et al. | | 5,899,425 A | 5/1999 | Corey, Jr. et al. |
| 5,363,850 A | 11/1994 | Soni et al. | | 5,904,659 A | 5/1999 | Duarte et al. |
| 5,366,465 A | 11/1994 | Mirza | | 5,957,814 A | 9/1999 | Eschenbach |
| 5,367,500 A | 11/1994 | Ng | | 5,962,790 A | 10/1999 | Lynnworth et al. |
| 5,376,065 A | 12/1994 | McLeod et al. | | 5,971,984 A | 10/1999 | Taylor et al. |
| 5,380,269 A | 1/1995 | Urso | | 5,997,490 A | 12/1999 | McLeod et al. |
| 5,386,830 A | 2/1995 | Powers et al. | | 6,019,710 A | 2/2000 | Dalebout et al. |
| 5,393,296 A | 2/1995 | Rattner | | 6,022,349 A | 2/2000 | McLeod et al. |
| 5,394,878 A | 3/1995 | Frazin et al. | | 6,030,386 A | 2/2000 | Taylor et al. |
| 5,398,290 A | 3/1995 | Brethour | | 6,050,943 A | 4/2000 | Slayton et al. |
| 5,400,795 A | 3/1995 | Murphy et al. | | 6,068,596 A | 5/2000 | Weth et al. |
| 5,405,389 A | 4/1995 | Conta et al. | | 6,080,088 A | 6/2000 | Petersen et al. |
| 5,409,446 A | 4/1995 | Rattner | | 6,086,078 A | 7/2000 | Ferez |
| RE34,959 E | 5/1995 | Potts | | 6,093,135 A | 7/2000 | Huang |
| 5,413,550 A | 5/1995 | Castel | | 6,165,144 A | 12/2000 | Talish et al. |
| 5,415,167 A | 5/1995 | Wilk | | 6,179,797 B1 | 1/2001 | Brotz |
| 5,417,215 A | 5/1995 | Evans et al. | | 6,206,843 B1 | 3/2001 | Iger et al. |
| 5,424,550 A | 6/1995 | Kawano et al. | | 6,213,958 B1 | 4/2001 | Winder |
| 5,431,612 A | 7/1995 | Holden | | 6,258,020 B1 | 7/2001 | Lopez |
| 5,434,827 A | 7/1995 | Bolorforosh | | 6,261,221 B1 | 7/2001 | Tepper et al. |
| 5,441,051 A | 8/1995 | Hileman et al. | | 6,261,249 B1 | 7/2001 | Talish et al. |
| 5,441,058 A | 8/1995 | Fareed | | 6,273,864 B1 | 8/2001 | Duarte et al. |
| 5,448,994 A | 9/1995 | Iinuma | | 6,355,006 B1 | 3/2002 | Ryaby et al. |
| 5,460,595 A | 10/1995 | Hall et al. | | 6,360,027 B1 | 3/2002 | Hossack et al. |
| 5,466,215 A | 11/1995 | Lair et al. | | 6,394,955 B1 | 5/2002 | Perlitz |
| 5,468,220 A | 11/1995 | Sucher | | | | |
| 5,476,438 A | 12/1995 | Edrich et al. | | FOREIGN PATENT DOCUMENTS | | |
| 5,478,306 A | 12/1995 | Stoner | | CA | 1328485 | 4/1994 |
| 5,492,525 A | 2/1996 | Gibney | | DE | 3639263 A1 | 6/1987 |
| 5,495,846 A | 3/1996 | Uehara et al. | | DE | 19613425 | 1/1997 |
| 5,496,256 A | 3/1996 | Bock et al. | | DE | 298 11 185 U1 | 12/1998 |
| 5,501,657 A | 3/1996 | Feero | | DE | 41 11 055 A1 | 10/2001 |
| 5,507,800 A | 4/1996 | Strickland | | EP | 0 181 506 A2 | 5/1986 |
| 5,507,830 A | 4/1996 | DeMane et al. | | EP | 331 348 A1 | 9/1989 |
| 5,509,933 A | 4/1996 | Davidson et al. | | EP | 0 536 875 A1 | 4/1993 |
| 5,520,612 A | 5/1996 | Winder et al. | | EP | 0 679 371 A1 | 11/1995 |
| 5,524,624 A | 6/1996 | Tepper et al. | | EP | 0 695 559 | 2/1996 |
| 5,526,815 A | 6/1996 | Granz et al. | | EP | 0 965 839 A1 | 12/1999 |
| 5,541,489 A | 7/1996 | Dunstan | | GB | 2156983 A | 10/1985 |
| 5,547,459 A | 8/1996 | Kaufman et al. | | GB | 2277448 A | 11/1994 |
| 5,556,372 A | 9/1996 | Talish et al. | | GB | 2 303 552 A | 2/1997 |
| 5,578,060 A | 11/1996 | Pohl et al. | | JP | SHO 62-47359 | 3/1987 |
| 5,615,466 A | 4/1997 | Safari et al. | | JP | HEI 4-82567 | 3/1992 |
| 5,626,554 A | 5/1997 | Ryaby et al. | | JP | HEI 4-82568 | 3/1992 |
| 5,626,630 A | 5/1997 | Markowitz et al. | | JP | HEI 4-82569 | 3/1992 |
| 5,630,837 A | 5/1997 | Crowley | | JP | HEI 5-269159 | 10/1993 |
| 5,648,941 A | 7/1997 | King | | WO | WO 85/03449 | 8/1985 |
| 5,656,016 A | 8/1997 | Ogden | | WO | WO 88/00845 | 2/1988 |
| 5,680,863 A | 10/1997 | Hossack et al. | | WO | WO 88/02250 | 4/1988 |
| 5,690,608 A | 11/1997 | Watanabe et al. | | WO | WO 90/06720 | 6/1990 |
| 5,691,960 A | 11/1997 | Gentilman et al. | | WO | WO 94/13411 | 6/1994 |
| 5,699,803 A | 12/1997 | Carodiskey | | WO | WO 95/03744 | 2/1995 |
| 5,702,353 A | 12/1997 | Guzzini et al. | | WO | WO 95/33416 | 12/1995 |
| 5,702,389 A | 12/1997 | Taylor et al. | | WO | WO 96/25112 | 8/1996 |
| 5,706,818 A | 1/1998 | Gondo | | WO | WO 96/25888 | 8/1996 |
| 5,708,236 A | 1/1998 | Shaanan et al. | | WO | WO 97/33649 | 9/1997 |
| 5,721,400 A | 2/1998 | Haraldsson et al. | | WO | WO 98/10729 | 3/1998 |
| 5,725,482 A | 3/1998 | Bishop | | WO | WO 98/34578 | 8/1998 |
| 5,728,095 A | 3/1998 | Taylor et al. | | WO | WO 98/47570 | 10/1998 |
| 5,730,705 A | 3/1998 | Talish et al. | | WO | WO 99/18876 | 4/1999 |
| 5,738,625 A | 4/1998 | Gluck | | WO | WO 99/22652 | 5/1999 |
| 5,741,317 A | 4/1998 | Ostrow | | WO | WO 99/48621 | 9/1999 |
| 5,743,862 A | 4/1998 | Izumi | | WO | WO 99/56829 | 11/1999 |
| 5,755,746 A | 5/1998 | Lifshey et al. | | WO | WO 99/58080 | 11/1999 |
| 5,762,616 A | 6/1998 | Talish | | | | |

| | | |
|---|---|---|
| WO | WO 00/03663 | 1/2000 |
| WO | WO 00/28925 | 5/2000 |
| WO | WO 00/67846 | 11/2000 |
| WO | WO 00/71207 | 11/2000 |
| WO | WO 00/76404 | 12/2000 |

OTHER PUBLICATIONS

ABSTRACT, (Proceedings of the 11th Int'l, Conference on Medical and Biological Engineering) "Ultrasonic Stimulation of Fracture Healing", 1976.
ABSTRACT, (Proceedings of the III Congress on Biomedical Engineering) "Ultrasonic Action on Callus Formation in Bones", 1975.
ABSTRACT, (Proceedings of the IV Brazilain Congress on Biomedical Engineering) "Ultrasound in the Treatment of Fractures", 1977.
ASTM Designation: D790M-93 Metric, "Standard Test Methods for flexural Properties of Unreinforced and Reinforced Plastics and Electrical Insulating Materials [Metric]", pp. 176-184, (Dec. 1993).
ASTM Designation: C1161-90, "Standard Test Method for Flexural Strength of Advanced Ceramics at Ambient Temperature," pp. 324-330. (Feb. 1991).
Brochure: "The Science Behind the Technology," distributed by Smith & Nephew for EXOGEN, no date.
Arai et al., "The Effect of Ultrasound Stimulation on Disuse Osteoporosis", BRAGS 17, 1993.
Berridge, M.J., "Inositol Trisphosphate and Calcium Signaling", *Nature* (1993), 361: 315-325.
Clarke, P.R. et al., "Physical and Chemical Aspects of Utrasonic Disruption of Cells", *JASA* (1969), 47(2): 649-653.
Duarte, L.R., "The Stimulation of Bone Growth by Ultrasound", *Arch. Orthop. Trauma Surg* (1983), 101: 153-159.
Dyson, M., "Therapeutic Applications of Ultrasound", *Biological Effects of Ultrasound* (1985), Nyborg, W.L. and Ziskin, M.C., eds; Churchill Livingstone Inc., New York, Chapter 11.
Goodship, A.E. et al., "The Influence of Induced Micromovement Upon the Healing of Experimental Tibial Fractures", *J. Bone and Joint Surg.* (1985), 67-B(4): 650-655.
Heckman, J.D. et al., "Acceleration of Tibial Fracture Healing by Non-Invasive Low-Intensity Pulsed Ultrasound", *J. Bone and Joint Surg.* (1994), 76-A(1): 26-34.
Hill, C.R., "Ultrasonic Exposure Thresholds for Changes in Cells and Tissues", *JASA* (1972), 52(2): 667-672.
Howkins, S.D., "Diffusion Rates and the Effect of Ultrasound", *Ultrasonics* (1969), 129-130.
Kristiansen, T.K. et al., "Accerlated Healing of Distal Radial Fractures with the Use of Specific, Low-Intensity Ultrasound", *J. Bone and Joint Surg.* (1997), 79-A(7) 961-973.
Maurice Hilario, "Low-Intensity Ultrasound Radiation in the Tissue Repair of Trophic Leg Ulcers", 1983, University of Sao Paulo, pp. 1-125.
Pethica, B.A., et al., Abstract, Biological Repair and Growth Society, Jun. 1998.
Phoenix (Business Wire), Jul. 8, 1997 via CompanyLink—OrthoLogic Corp.
"Reflex Sympathetic Dystrophy, Does RSD Exist?" www.arbon.com (Jun. 4, 1997).
"Reflex Sympathetic Dystrophy: The Pain That Doesn'T Stop," tcc.cc.nc.us (Jun. 4, 1997).
RSDnet.org "Reflex Sympathetic Dystrophy," www.rsdnet.org (Jun. 4, 1997).
Ter Haar, G., et al., "Basic Physics of Therapeutic Ultrasound", *Physiotherapy* (1987), 73(3): 110-113.
Yang K.H. et al., "Exposure to Low-Intensity Ultrasound Treatment Increases Aggrecan Gene Expression in a Rat Femur Fracture Model", *J. Ortho Research* (1996), 14:802-809.
Treatment of Osteochondral Defects in Rabbits with SAFHS—Part I and II, EX1095-01R, EX1096-01R.
Treatment of Osteochondral Defects in Rabbits with SAFHS—Part III, EX1097-01R (Aug. 26, 1997).

Cook, Stephen and L. Patron, "Treatment of Osteorchondral Defects in Rabbits with SAFHS—A Mosaicplasty Model"—Final Report, EX1098-04R (Aug. 12, 1999).
Acoustic Emission—An Update, by Arthur E. Lord, Jr., 1981, Physical Acoustics, vol. XV, pp. 295-360.
Acoustic Emission and Diagnosis of Osteoporosis, by S. Hanagud, G. T. Hannon and R. Clinton, 1974, Ultrasonic Symposium Proceedings (IEEE), pp. 77-81.
Acoustic Emission in Bone Substance, by S. Hanagud, R.G. Clinton and J.P. Lopez, 1973, Biomechanics Symposium Proceedings (ASME), pp. 79-81.
Acoustic Emission Inspection, by Adrian A. Pollock, 1992, ASM Handbook, vol. 17, Nondestructive Evaluation and Quality Control, pp. 278-293.
Acoustic Emission Techniques in the Development of a Diagnostic Tool for Osteoporosis, by S. Hanagud and R. G. Clinton, 1975, Ultrasonic Symposium Proceedings (IEEE), pp. 41-45.
Application of an intelligent signal processing system to acoustic emission analysis, by Igo Grabec and Wolfgang Sachse, Mar. 1989, Acoustic Society of America, pp. 787-791.
Application of correlation techniques for localization of acoustic emission sources, by I. Grabec, 1978, IPC Business Press Ltd., pp. 111-115.
Cornejo, et al., "Large-Area Flexible-Array Piezoelectric Ceramic/Polymer composite Transducer for Bone Healing Acceleration," presented at ISAFXI, Montreux, Switzerland (1998).
Clough, R. and J. Simmons, "Theory of Acoustic Emission," Metallurgy Division, national Bureau of Standards, no date.
Fritton, et al., "Whole-Body Vibration in the Skeleton: Development of a Resonance-Based Testing Device," *Annals of Biomedical Engineering*, vol. 25, pp. 831-839 (1997).
Goodship, et al., "Low magnitude high frequency mechanical stimulation of endochondral bone repair" 43rd Annual Meeting Orthopeadic Research Society, vol. 22, Sec. 1, Feb. 9-13, (1997).
J. Kenwright, et al., "Controlled Mechanical Stimulation in the Treatment of Fibial Fractures," Orthopedics, Clinical Orthopedics and Related Research (1989) 241:36-47.
Jankovich, "The Effects of Mechanical Vibration on Bone Development in the Rat," *J. Biomechanics*, 1972, vol. 5, pp. 241-250.
Ko, "Preform Fiber Architecture for Ceramic-Matrix Composites," Ceramic Bulletin, vol. 68, No. 2, pp. 401-414(1989).
McLeod, et al., "Improved Postural Stability Following Short Term Exposure to Low Level Whole Body Vibration," 44th Annual Meeting, Orthopaedic Research Society, Mar. 16-19, 1998, New Orleans, Louisiana, pp. 89-15.
Newnham, et al., Connectivity and Piezoelectric-Pyroelectric Composites, Med. Res. Bull., vol. 13, pp. 525-536 (1978).
Pauer, "Flexible Piezoelectric Material," pp. 1-5, no date.
Pilgrim, et al., "An Extension of the Composite Nomenclature Scheme," Med. Res. Bull., vol. 22, pp. 877-894 (1987).
Powell, et al., "A Performance Appraisal of Flexible Array Structures Using a Facet Ensemble Scattering Technique," *1991 Ultrasonic Symposium*, pp. 753-766.
Powell, et al., "Flexible Ultrasonic Transducer Arrays for Nondestructive Evaluation Applications—Part II: Performance Assessment of different Array Configurations," *IEEE Transactions on Ultrasonics*, Ferroelectrics, and Frequency Control, vol. 43, No. 3, May 1996, pp. 393-402.
Sarvazyan, "Some General Problems of Biological Action of Ultrasound," IEEE Transactions on Sonics and Ultrasonics, vol. 30, No. 1, Jan. 1983.
Ultrasound as a Tool for Investigating Bone: Fundamental Principles and Perspectives for Use in Osteoporosis, by J. G. Bloch, 1993, Expanson Scientifique Francaise.
Y. Qin, et al., "Correlation of In Vivo Bone Adaptation and Mechanical Parameters Using Low Magnitude, High Frequency Loading," 41st Annual Meeting Orthopaedic Research Soc., vol. 20—Sec. 1, Feb. 13-16 (1955).
Bascom, "Other Continuous Fibers," 118/Constitutent Material Form.
Bascom, "Other Discontinuous Forms," 120/Constituent Material Forms.

Cass, "Fabrication of Continuous Ceramic Fiber by the Viscous Suspension Spinning Process," *Ceramic Bulletin*, vol. 70, No. 3, pp. 424-429 (1991).

"Development of Flexible Pieoelectric Transducers and Matching Layers for EXOGEN Incorporated," Final Report, Covering Period Apr. 1, 1997 to Feb. 28, 1998, Rutgers University.

Grewe, et al., "Acoustic Properties of Particle Polymer Composite for Ultrasonic Transducer Backing Applications," *IEEE*, (1990).

Grewe, Martha G., "Acoustic Matching And Backing Layer for Medical Ultrasonic Transducers," A Thesis in Solid State Science, The Pennsylvania State University; (May 1989), The Center for Ceramics Research, Rutgers.

Gururaja, T., "Piezoelectric Composite Materials for Ultrasonic Transducer Applications," A Thesis in Solid State Science, The Pennsylvania State University, May 1984.

Gururaja, "Piezoelectrics for Medical Ultrasonic Imaging," *Am. Ceram. Soc. Bull.*, vol. 73, No. 5, pp. 50-55 (May 1994).

Hall, et al., "The design and evaluation of ultrasonic arrays using 1-3 connectivity composites," *SPIE*, pp. 216-227, vol. 1733 (1992).

Niemczewski, B., "A Comparison of Ultrasonic Cavitation Intensity in Liquids," *Ultrasonics*, vol. 18, pp. 107-110, 1980.

Pilla, et al., "Non-Invasive Low-Intensity Pulsed Ultrasound Accelerates Bone Healing in the Rabbit," *Journal of Orthopaedic Trauma*, vol. 4, No. 3, pp. 246-253 (1990).

Safari, "Development of piezoelectric composites for transducers," *J. Phys.France*, 4:1129-1149 (1994).

Selfridge, "Approximate Material Properties in Isotropic Materials," *IEEE Transactions on Sonics and Ultrasonics*, May 9, 1985).

Souquet, et al., "Design of Low-Loss Wide-Band Ultrasonic Transducers for Noninvasive Medical Application," *IEEE Transactions on Sonics and Ultrasonics*, pp. 75-81, vol. SU-26, No. 2, Mar. 1979.

Waller, et al., "Poling of Lead Zirconate Titanate Ceramics and Flexible Piezoelectric Composites by the Corona Discharge Technique," *J. Am. Ceram. Soc.*, 72(2):322-24 (1989).

Winder, Alan, "Synthetic Structural Imaging and Volume Estimation of Biological Tissue Organs," ,Acoustic Sciences Associates, Dec. 1995.

Winder, Alan, "Acoustic Emission Monitoring for the Detection, Localization and Classification of Metabolic Bone Disease," Acoustic Sciences Associates, Dec. 1995.

Wu and Cubberly, " Measurement of Velocity and Attenuation of Shear Waves in Bovine Compact Bone Using Ultrasonic Spectroscopy," Med. & Biol., vol. 23, No. 1,129-134, 1997.

Tavakoli and Evans , "The Effect of Bone Structure on Ultrasonic Attenuation and Velocity," *Ultrasonics*, vol. 30, No. 6 (1992).

\* cited by examiner

ULTRASOUND BANDAGES

This application claims benefit of Ser. No. 60/084,453 filed May 6, 1998.

BACKGROUND OF THE INVENTION

1. Field of the Invention

Novel ultrasound bandages and ultrasound transducer array bandages are described herein. Also described are methods for manufacturing the ultrasound bandages and ultrasound transducer array bandages. Additionally, use of the ultrasound bandages and ultrasound transducer array bandages in medical therapeutic ultrasound applications, e.g., for promoting the healing of wounds, i.e., wound healing, such as abrasions, lacerations, incisions and venous ulcers, are also described herein.

2. Description of the Related Art

The therapeutic value of ultrasonic waves is known. For example, U.S. Pat. No. 4,530,360 to Duarte describes a basic non-invasive therapeutic technique and apparatus for applying ultrasonic pulses externally on the skin of the patient at a location adjacent to a bone fracture site. The applicator described in the '360 patent has a plastic tube which serves as a grip for the operator, an RF plug attached to the plastic tube for connection to an RF source, and internal cabling connected to a rigid ultrasonic transducer. To apply the ultrasonic pulses during treatment, an operator manually holds the applicator in place until the treatment is complete. The '360 patent also describes a range of RF signals for creating the ultrasound, ultrasound power density levels, a range of duration for each ultrasonic pulse, and a range of ultrasonic pulse frequencies.

As another example, U.S. Pat. Nos. 5,003,965 and 5,186,162, both to Talish and Lifshey, describe an ultrasonic body treatment system in which the RF generator and transducer are both part of a modular applicator unit which is placed at the skin location. Both the '965 and '162 patents are concerned with healing, for example, bone fractures by placing the body treatment system within a cast and then surrounding the treatment site with the cast.

Yet another example is U.S. Pat. No. 5,211,160 to Talish and Lifshey which describes a bandage assembly which is mounted on uncovered body parts, i.e., without a cast or other medical wrapping. The bandage assembly is typically wrapped around the region of the body, e.g., the leg, being subjected to ultrasonic therapy with a treatment head unit containing an ultrasonic transducer being removably assembled to the bandage assembly during treatment.

While these prior art systems provide accelerative healing of soft tissue wounds and bone fractures, none of the systems provide an ultrasound bandage having an adhesive layer with a transducer material disposed thereon for treatment of wounds.

Previous attempts have been made to provide a bandage having a transducer material. For example, U.S. Pat. No. 4,787,888 discloses a bandage assembly for percutaneous administration of a medicament. The bandage assembly described in the '888 patent has a bandage member with a cavity containing a medicament and having two transducer materials, e.g., piezoelectric polymers, extending thereacross with a pair of electrical contacts disposed adjacent the opposite surfaces of the transducer material. The transducer materials, however, are employed to produce sonic vibrations in the material from a sonic generator to stretch the pores of the skin thereby inducing the medicament into the pores for therapeutic treatment.

It would be desirable to provide an ultrasound bandage having an adhesive layer with a transducer material disposed on at least a portion thereof such that the bandage can be applied to the portion of the skin at or near a wound by way of the adhesive layer and the transducer material facilitating the transfer of acoustic energy during each therapeutic application to promote the healing of the wound with the ultrasound bandage being discarded upon completion of each application.

SUMMARY OF THE INVENTION

Novel ultrasound bandages and ultrasound transducer array bandages for use in therapeutic applications have been discovered. In one embodiment, the novel ultrasound bandages include at least a backing layer, an adhesive layer applied to, and substantially coextensive with, the backing layer, and a transducer material disposed on at least a portion of the adhesive layer. Electrode surfaces can be applied to opposite surfaces of the transducer material with a matching layer being applied to, and substantially coextensive with, the electrode surface not applied to the adhesive layer. A coupling pad can then be applied to, and substantially coextensive with, the matching layer.

In another embodiment, an ultrasound transducer array bandage is formed by disposing on at least a portion of an adhesive layer which is applied to, and substantially coextensive with, a backing layer, an array comprised of a plurality of transducer materials arranged in adjacent relation to define spaces therebetween. Electrode surfaces ban be applied to opposite surfaces of each transducer material with a matching layer being applied to, and substantially coextensive with, the electrode surface not applied to the adhesive layer. A coupling pad can then be applied to, and substantially coextensive with, the array.

A method for making the ultrasound bandage has also been discovered. In the method, an adhesive layer is applied to, and substantially coextensive with, a backing layer, and a transducer material is disposed on at least a portion of the adhesive layer.

A method for making an ultrasound transducer array bandage has also been discovered. In the method, an adhesive layer is applied to, and substantially coextensive with, a backing layer, a plurality of transducer materials are arranged in adjacent relation to define spaces therebetween to form an array, the array being disposed on at least a portion of the adhesive layer, and, optionally, a coupling pad is applied to, and substantially coextensive with, the array.

A method for using the ultrasound bandage or ultrasound transducer array bandage in therapeutic applications has also been discovered. In the method, the ultrasound bandage or ultrasound transducer array bandage can be applied to a wound on the human anatomy or, alternatively, adjacent to the wound, in need of therapeutic stimulation and that section of the human anatomy is then exposed to a dosage amount of acoustic energy.

The term "wound" for the purposes of "wound healing" shall be understood herein to include ulcers such as venous ulcers, burns, ulcerated wounds due to, for example, diabetes, incisions such as surgical incisions or other surgical cuttings including stitched surgical cuttings, skin grafts, hair transplants, revascularization, bed sores, tissue dehiscence, ligament and tendon repair and reconstruction, abrasions and lacerations.

The ultrasound bandages and ultrasound transducer array bandages described herein possess at least an adhesive layer having at least one transducer material disposed on at least a portion thereof to advantageously permit acoustic energy generated by the transducer(s) to be efficiently applied and coupled to the contours of the human anatomy for therapeutic applications. Additionally, after each application of therapeutic treatment, the ultrasound bandages and ultrasound transducer array bandages can be conveniently discarded with a new bandage being applied to the human anatomy for the next therapeutic application.

BRIEF DESCRIPTION OF THE DRAWINGS

Preferred embodiments of the invention are described below with reference to the drawings, which are described as follows.

DESCRIPTION OF THE PREFERRED EMBODIMENTS

Figure 1:
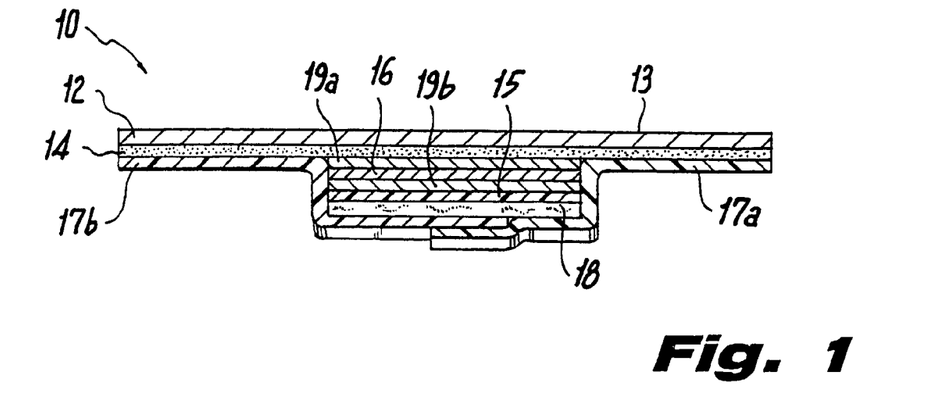
FIG. 1 is a schematic cross-sectional view of an ultrasound bandage in accordance with the present invention.

One embodiment of an ultrasound bandage in accordance with the present invention is shown generally in FIG. 1 at 10. In general, the ultrasound bandage includes a backing layer 12 possessing upper and lower surfaces. Adhesive layer 14 is applied to, and substantially coextensive with, lower surface 13 of backing layer 12 for securing the ultrasound bandage 10 to the skin of the patient. Transducer material 16 can be disposed on at least a portion of adhesive layer 14 or, alternatively, transducer material 16 can be applied within at least a portion of adhesive layer 14. In this way, transducer material 16 can be removed, if desired, prior to disposal of ultrasound bandage 10 after use. Electrode surfaces 19a and 19b can be applied to, and substantially coextensive with, opposite surfaces of transducer material 16. Matching layer 15 can be applied to, and substantially coextensive with, electrode surface 19b. Coupling pad 18 can be applied to, and substantially coextensive with, matching layer 15, thereby providing an efficient coupling path between the transducer material 16 and the patient's skin and soft tissue for delivery of acoustic energy to the wound in need of therapeutic treatment. Alternatively, coupling pad 18 can include end portions (not shown) which extend beyond and fold over matching layer 15 to adhere to adhesive layer 14. Release liners 17a and 17b seal and protect adhesive layer 14, transducer material 16 and coupling pad 18 during the residency of ultrasound bandage 10 within its package with release liner 17a overlapping release liner 17b.

In general, backing layer 12 can be any material, woven or non-woven, synthetic or natural, porous or non-porous, perforated or non-perforated, elastic or non-elastic, which will provide support and act as a protective covering for the bandage 10. Suitable materials include, for example, cellophane, cellulose acetate, ethyl cellulose, plasticized vinyl acetate-vinyl chloride copolymers, ethylene-vinyl acetate copolymer, polyethylene terephthalate, nylon, polyethylene, polypropylene, polyvinylidene, chloride, paper, cloth, aluminum foil and the like. Preferably, backing layer 12 is a moisture vapor permeable, liquid impermeable flexible thin film or sheet with the thin film being more preferred. A preferred thin film for use herein is a polyurethane film. If desired, the backing layer 12 can be fabricated from a composite of films. The composite can be a metallized, e.g., aluminized, film or a laminate of two or more films or a combination thereof. For example, a laminate of polyethylene terephthalate and polyethylene or a polyethylene/metallized polyethylene terephthalate/polyethylene laminate can be employed. Useful polymers include polyethylene, polypropylene, polyvinyl chloride, polyethylene terephthalate and the like. The width and thickness of backing layer 12 will vary according to the size of the bandage employed and are conventional in the art. Therefore, these widths and thicknesses need not be discussed in detail herein.

Adhesive layer 14 of bandage 10 is preferably a pressure sensitive adhesive layer and can be selected from any of the known and conventional medical grade adhesives, e.g., those based on polyacrylic, polyvinylether, or polyurethane resins. Useful pressure sensitive adhesives include those disclosed in U.S. Pat. No. 4,573,996, the contents of which are incorporated by reference herein. It is an essential requirement that the amount of adhesive layer 14 applied to lower surface 13 of backing layer 12 be sufficient to achieve an acceptable level of adhesion of ultrasound bandage 10 to the skin and to apply and adhere transducers 16. Thus, the various shapes and sizes of adhesive layer 14 will depend, for example, on the area of a patient's body to which they are applied, the size and weight of transducer material 16, the size and shape of the external wound, etc. The amount of adhesive that will satisfy this criteria can be readily determined by simple and routine testing. Ordinarily, a medical grade adhesive applied to a thickness ranging from about 1.0 mils to about 3.5 mils and preferably from about 2.0 mils to about 2.5 mils (depending, of course, on the thickness of the backing layer) will meet this requirement reasonably well. Adhesive layer 14 may include holes or a permeable material to allow moisture to escape and provide oxygen to the skin.

Transducer material 16 can be formed from any transducer material known to one skilled in the art, e.g., an air backed quarter wave matched transducer material, polyvinyledene fluoride material (PVDF), etc. Preferably, transducer material 16 can be those disclosed in International PCT Application No. PCT/US99/06650, filed on Mar. 26, 1999, the contents of which are incorporated by reference herein. For example, transducer material 16 can be formed from one or more fibers extruded from a composition containing a piezoelectric material. The extruded fibers can be knitted, woven or braided in 1, 2 or 3 dimensions to provide a structure that includes spaces which can be filled with a polymeric material to form a composite. Fibers made of piezoelectric material suitable for use herein can be prepared, for example, by using a viscous suspension spinning process and are available from Advanced Cerametrics Incorporated (Lambertville, N.J.). Suitable piezoelectric materials for use in the fibers include PZT powders commercially available from Morgan Matroc, Inc., ceramic, lead zirconate titanate $Pb(Zr,Ti)O_3$ lead metaniobate $Pb(Nb_2O_6)$, modified lead titanate $PbTi_3$ such as $(Pb,Ca)TiO_3$ and $(Pb, Sm)TiO_3$, barium titanate $BaTiO_3$, PMN—PT$(1-x)Pb(Mg_{1/3},Nb_{2/3})O_3$-$xPbTiO_3$, PZN—PT/BT $Pb(Zn_{1/3},Nb_{2/3})O_3$-$xPbTiO_3$—$BaTiO_3$, $(1-x)Pb(Zn_{1/3},Nb_{2/3})O_3$-$x(yPbTiO_3$-$(1-y)PbZrO_3)$ and the like. In particularly useful embodiments, the extruded fibers are knitted, woven, braided or non-woven to form a fiber sheet. Preferably, a simple woven fabric is used as the fiber sheet. Optionally, the individual fibers in the fiber sheets can be coated with a film-forming polymer solution to improve the strength and wear resistance of the individual fibers prior to weaving, knitting and braiding. Suitable solutions of film-forming material are known to those in the textile art. By way of example, the solution can contain a mixture of a polyvinyl alcohol and polyvinyl acetate as a major component thereof and polyethylene glycol as a minor component thereof.

Transducer material 16 can be of varying shapes and sizes depending, of course, on the size of the wound to be treated. This can be determined according to simple and routine experimental testing. Ordinarily, the thickness of transducer material 16 will range from about 0.1 mils to about 5 mils and preferably from about 1.5 mils to about 3.0 mils with the width of material 16 ranging from about 0.1 inch to about 1.5 inches and preferably from about 0.5 inch to about 1 inch.

Electrode surfaces 19a and 19b are applied to opposite surfaces of transducer material 16. Typically, electrode surface 19a will be applied onto one surface of the transducer material by techniques known to one skilled in the art, e.g., utilizing photolithographic techniques. In general, electrode surface 19b will be applied to, and substantially coextensive with, the other surface of the transducer material. Electroding can be achieved employing techniques known to one skilled in the art, e.g., sputtering, painting. Materials useful in forming the electrode surfaces include copper, silver, nickel, gold, alloys, mixtures thereof and the like. Typically, electrode surface 19a will be positively charged and the other electrode surface 19b will serve as a ground.

Once electrode surfaces 19a and 19b have been applied, matching layer 15 can then be applied to, and substantially coextensive with, electrode surface 19b. Techniques for applying the matching layer are within the purview of one skilled in the art. Generally, the thickness of the matching layer can be chosen to correspond to one-quarter of the wavelength in the matching layer at the operating frequency of the transducer array. The acoustic impedance of the matching layer will preferably range from about 2.0 to about 7.0 MRayls.

Matching layer 15 will ordinarily be formed from a polymeric material, and optionally, a filler. The polymeric material should have good compatibility with the components of the composite, biocompatibility and flexibility. Useful polymeric materials include thermoplastics such as high density polyethylenes, polymethyl methacrylates, polypropylenes, polybutylene terephthalates, polycarbonates, polyurethanes such as CA 118 and CA 128 available from Morton Chemical and estane polyester, and the like; thermosets such as epoxies such as Spurr epoxy and Stycast 80, and the like; and rubbers such as silicone rubbers such as dispersion 236 available from Dow Corning and RTV-141 available from Rhone-Poulenc, Inc. and the like. A preferred polymeric material for use herein is Stycast 1365-65. Because the acoustic impedance of many polymeric materials is less than the preferred range of 2.0–7.0 MRayls, it is necessary to increase the acoustic impedance of the polymer. Accordingly, one or more fillers can be incorporated therein. Suitable fillers include PZT, tungsten, alumina, silica glass, tungsten carbide, titanium, glass powder and the like with glass powder being preferred. The size of the filler particles should be in the range of about 0.1 to about 50 microns and preferably from about 0.5 to about 5 microns. The amount of filler employed will be that amount necessary to impart the desired acoustic impedance. Normally, from about 2 to about 50 percent filler by volume and preferably from about 5 to about 30 volume percent filler is employed.

Figure 2A:
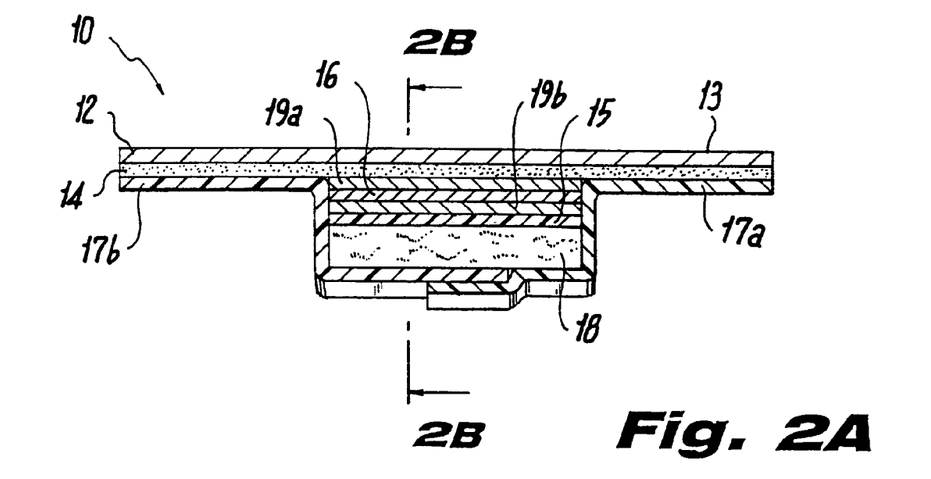
FIG. 2A is a schematic cross-sectional view of the ultrasound bandage of FIG. 1 with a thicker coupling material.
Figure 2B:
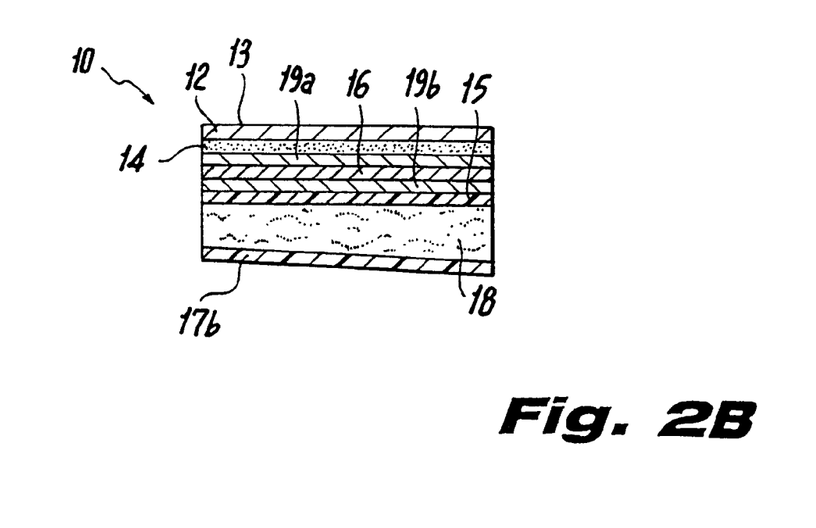
FIG. 2B is a schematic transverse cross-sectional view of the ultrasound bandage of FIG. 2A taken along axis 2B—2B illustrating the coupling material configured as a wedge.

Coupling pad 18 can be selected from any coupling material known to one skilled in the art. A preferred coupling material for use herein is a hydrogel pad. Coupling pad 18 can have a substantially planar surface as depicted in FIG. 1. Alternatively, coupling pad 18 can be configured, for example, as a wedge, i.e., possessing a non-planar surface, as depicted in FIG. 2A and FIG. 2B. Thus, when employing a coupling pad 18 configured as, for example, a wedge, the longitudinal waves are to be transmitted from the transducer off-axis, at an angle equal to or slightly greater than the critical angle, depending on Poisson's ratio for soft tissue, where the longitudinal waves are converted completely into shear waves (modal conversion) for therapeutic ultrasonic stimulation and treatment at the site of the wound.

Since the delivery of ultrasound to a target injury requires an efficient coupling path between the transducer material and the patient's skin and soft tissue, a material for ultrasound coupling is typically employed to effect a proper interface for propagating acoustic energy into the patient's body. Commonly used materials include sonically conductive materials such as, for example, glycerol, water, oils, lotions, etc., which are applied onto the coupling pad prior to bandage 10 being placed on the patient's body.

Figure 3:
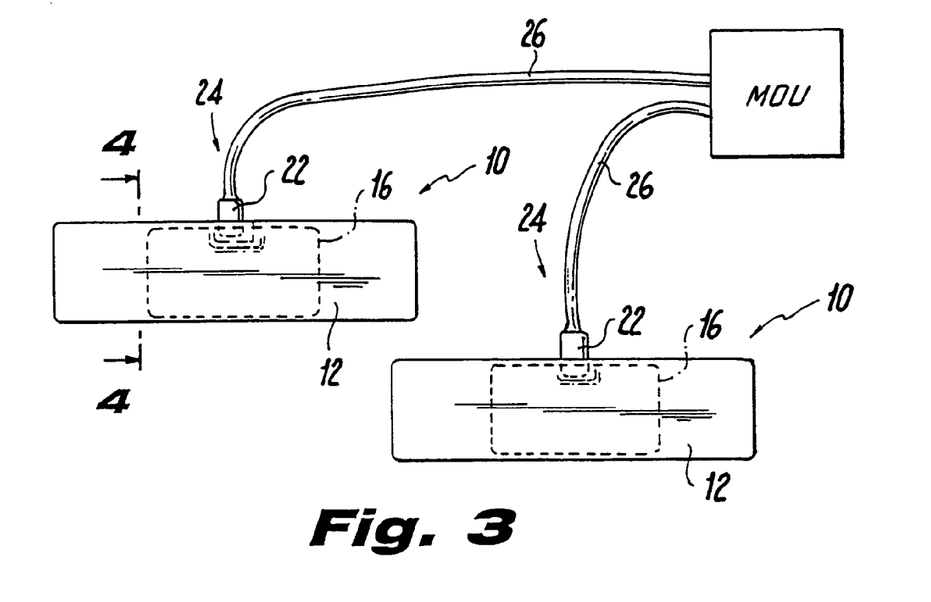
FIG. 3 is a schematic top view of the ultrasound bandage of FIG. 1 in an assembly.
Figure 4:
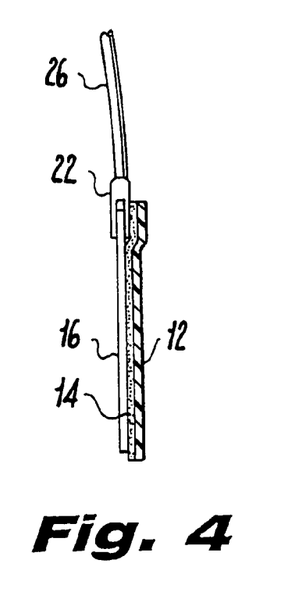
FIG. 4 schematic side view of the ultrasound bandage assembly of FIG. 3 in accordance with the present invention.

Ultrasound bandage 10 is typically employed in an ultrasound bandage assembly as generally depicted in FIG. 3. Ultrasound bandage assembly 20 will include at least one or more ultrasound bandages 10 having connector assemblies 24 with leads 26 for coupling ultrasound transducers 16 to a portable main operating unit (MOU). Connector assemblies 24 include detachable connectors 22 for detachably connecting leads 26 to transducers 16 which is mounted on adhesive layer 14 (see FIG. 4). Connectors 22 are operatively coupled to transducers 16 and are preferably of the quick-connected type such that leads 26 may be detached and reused while ultrasound bandages 10 can be disposed of. The MOU supplies powers and provides signals for controlling transducers 16. In one embodiment, the MOU can be a commercially available device such as, for example, an SAFHS 2000 available commercially from Exogen, Inc. (Piscataway, N.J.). A preferred MOU is described in further detail in U.S. application Ser. No. 09/040,157 which is incorporated by reference herein. The MOU preferably includes a processor which could be a microprocessor used in conjunction with transducers 16. The processor generates control signals which are amplified by an output driver to the desired power level and imparted to the transducers 16.

Figure 5:
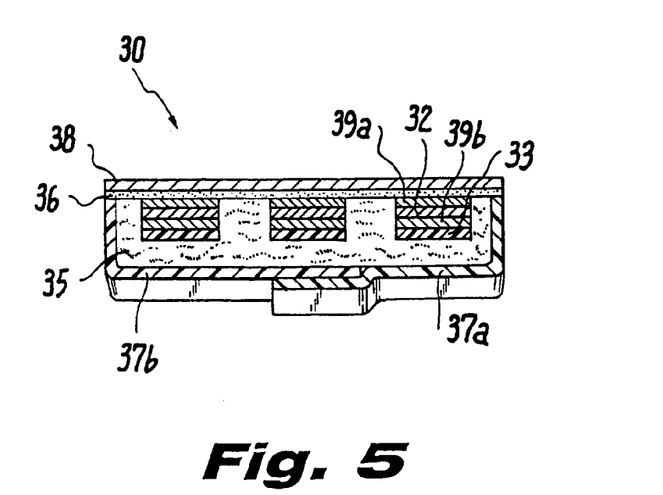
FIG. 5 schematic cross-sectional view of a ultrasound transducer array bandage in accordance with the present invention.

The ultrasound transducer array bandages of the present invention can be obtained by forming an array of a plurality of the foregoing transducer materials. The transducer array bandage 30 can be formed, for example, by disposing an arrangement of transducer materials 32 in adjacent relation to one another to define spaces 34 therebetween as generally depicted in FIG. 5. It is to be understood that the transducer materials 32 can be of varying sizes when forming the array bandage described herein. In general, the transducer materials 32 can be placed close together or spaced further apart and the spacings need not be uniform or in perfect alignment.

The transducer materials 32 are disposed on or within at least a portion of adhesive layer 36 which is applied to, and substantially coextensive with, backing layer 38. Useful materials for forming backing layer 38 and adhesive layer 36 can be any of the aforementioned materials. Typically, the spaces between transducer materials 32 will range from about 0.5 mm to about 10 mm and preferably from about 1 mm to about 3 mm. The dimensions of the array will ordinarily range from about 0.5 inch to about 6 inches wide and from about 0.5 inch to about 12 inches long. The thickness of the array can effect the frequency of operation and will ordinarily range from about 0.05 mm to about 10 mm. It should, of course, be understood that the array can include transducer materials with different frequencies of operation. These differences in frequency of operation can be achieved by employing transducer materials of different thicknesses.

Electrode surfaces 39a and 39b can be applied to, and substantially coextensive with, each transducer material 32 in the array. Once the electrode surfaces have been applied, matching layers 33 can then be applied to, and substantially coextensive with, electrode surfaces 39b. Useful materials for forming the electrode surfaces and the matching layer can be any of the aforementioned materials.

Figure 6A:
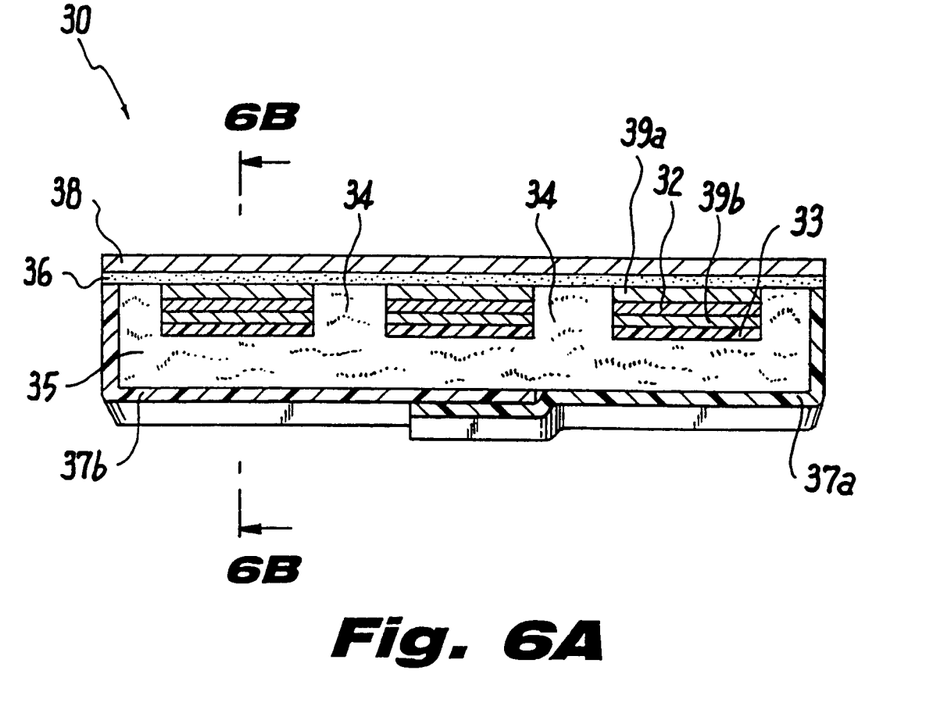
FIG. 6A is a schematic cross-sectional view of the ultrasound transducer array bandage of FIG. 5 with a thicker coupling material.
Figure 6B:
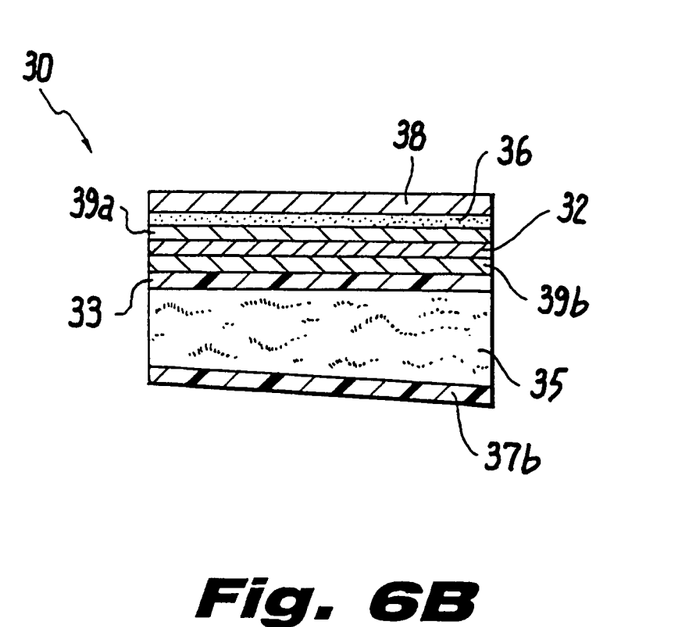
FIG. 6B is a schematic transverse cross-sectional view of the ultrasound transducer array bandage of FIG. 6A taken along axis 6B—6B illustrating the coupling material configured as a wedge.

Coupling pad 35 can be, for example, a hydrogel pad, and is typically applied to, and substantially coextensive with, each matching layer 33, i.e., the array. Alternatively, coupling pad 35 can be applied to, and substantially coextensive with, each matching layer 33 (not shown). In use, coupling pad 35 can have a substantially planar surface as depicted in FIG. 5. Alternatively, coupling pad 35 can be configured, for example, as a wedge, i.e., possessing a non-planar surface, as depicted in FIG. 6A and FIG. 6B. Thus, when employing a coupling pad 35 configured as, for example, a wedge, the longitudinal waves are to be transmitted from the transducers off-axis, at an angle equal to or slightly greater than the critical angle, depending on Poisson's ratio for soft tissue, where the longitudinal waves are converted completely into shear waves (modal conversion) for therapeutic ultrasonic stimulation and treatment at the site of the wound. Release liners 37a and 37b seal and protect adhesive layer 36, transducer materials 32 and coupling pad 35 during the residency of ultrasound transducer array bandage 30 within its package with release liner 37a overlapping release liner 37b.

Figure 7:
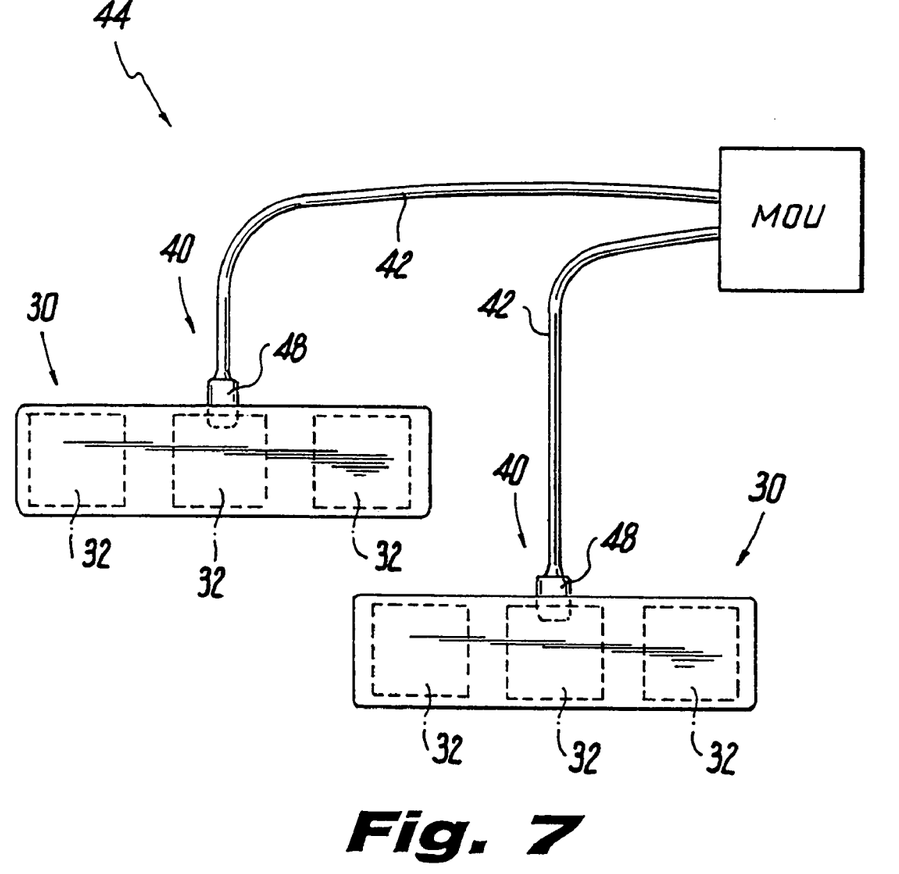
FIG. 7 is a schematic top view of the ultrasound transducer array bandage of FIG. 5 in an assembly.

Once the ultrasound transducer array bandage 30 has been formed, connector assemblies 40 with leads 42 for coupling ultrasound transducers 32 to a portable main operating unit (MOU) are applied to the transducers 32 to form an ultrasound transducer array bandage assembly 44 as generally depicted in FIG. 7. Connector assemblies 40 include detachable connectors 48 for detachably connecting leads 42 to transducers 32 which is mounted on adhesive layer 36. Connectors 48 are operatively coupled to transducers 32 and are preferably of the quick-connected type such that leads 42 may be detached and reused while ultrasound transducer array bandages 44 can be disposed of.

The ultrasound bandages and ultrasound transducer array bandages of this invention can also possess a protective covering (not shown) instead of release liners 17a and 17b and 37a and 37b, respectively. Covers of this kind are known from U.S. Pat. No. 4,627,429, the contents of which are incorporated by reference herein. In general, the protective covering can be made, for example, of a heat-sealable aluminum foil film laminate with the heat-sealable surface down. A formed cup, dome or square in the cover allows room for the transducer materials and coupling pad with the other portion of the cover being placed over the adhesive layer.

Figure 8:
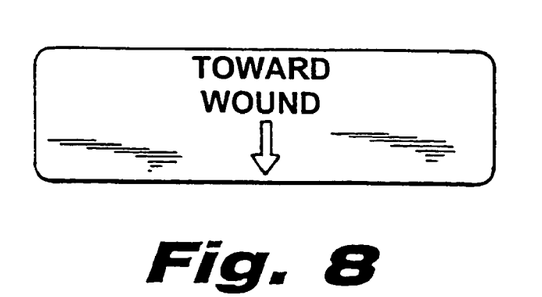
FIG. 8 is a schematic top view of ultrasound bandage possessing indicia thereon.

The ultrasound bandages and ultrasound transducer array bandages of this invention can be manufactured in a variety of sizes and shapes, e.g., rectangular, oval, etc., and can be planar or three-dimensional. Additionally, the ultrasound bandages and ultrasound transducer array bandages used herein can contain indicia thereon, e.g., text, color, etc., to indicate the direction of the transducer so that the ultrasonic waves can be directed toward the wound as depicted in FIG. 8.

The ultrasound bandages and ultrasound transducer array bandages of this invention are particularly useful in therapeutic applications. In general, the foregoing bandages will be applied adjacent to, or directly over, the wound to facilitate the transfer of acoustic energy to promote the healing of wounds. As noted above, the term "wound" as used herein has a broad meaning as generally encompassing addressing damage to, and repair of, or restoration of soft tissue or wounds to the skin such as abrasions and lacerations. The present invention can be used, for example, to prevent surgical adhesions by stimulating the proper repair of surgical incisions. It can also prevent or arrest wound dehiscence by promoting vascularization at the surfaces adjacent surgical incisions. It can also be used in cosmetic surgery, for example, by enhancing the healing of hair transplants, or by directly stimulating regeneration of cells.

In general, once the acoustic energy enters the body, it passes into internal body tissue and/or fluids. The acoustic energy, in the form of ultrasonic pulses, is reflected off the surface of underlying bone or other ultrasound reflective material and the reflected ultrasound travels toward at least part of the internal surface or underside of the wound. Healing of the wound at the internal surface by the generation of epithelial cells is enhanced via the acoustic stimulation.

Preferably, a low frequency signal which is present as the modulation of the carrier frequency is transmitted as a longitudinal acoustic wave from the transducer material, through interposed soft tissue, and onto the surface of the bone. The longitudinal wave incident on the bone surface, or other designated reflection sites in the body, is reflected toward the internal surface of the wound as longitudinal and/or shear waves. These reflected waves flooding a region of the internal surface of the wound increase vascularization at the internal surface of the wound thus enhancing growth of epithelial cells. The epithelial cell growth represents healing of the wound. The technique thus promotes healing of the wound from the internal surface of the wound.

Figure 9:
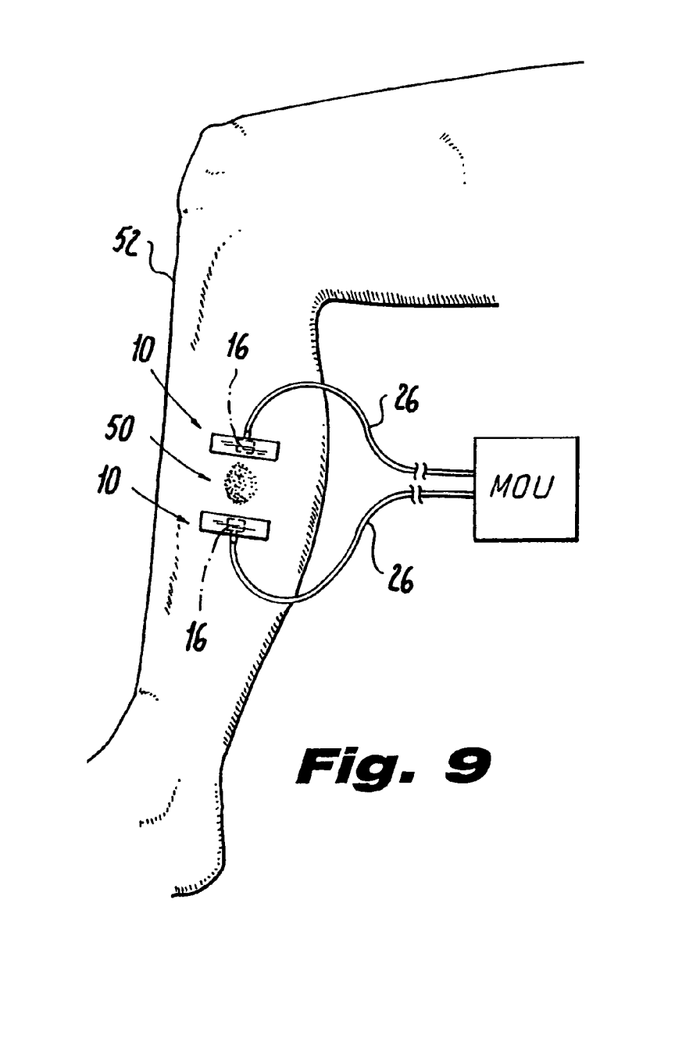
FIG. 9 is a perspective view of the ultrasound bandage assembly of FIG. 3 in use in accordance with the present invention; and, FIG. 10 is a perspective view of the ultrasound transducer array bandage of FIG. 5 in use in accordance with the present invention.
Figure 10:
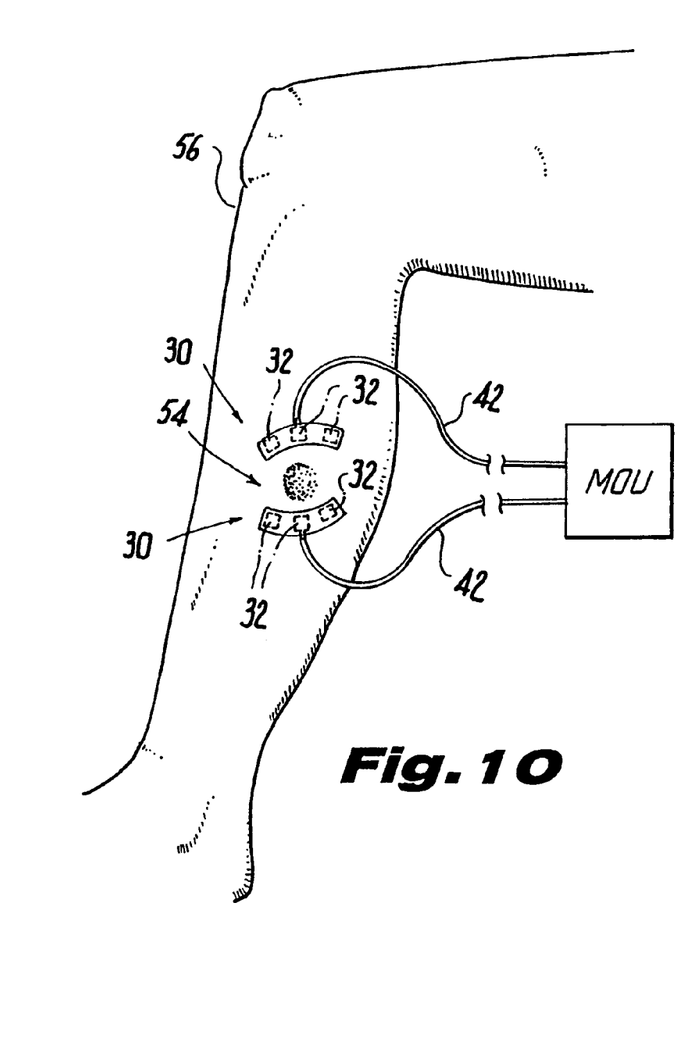

The number, position and size of ultrasonic bandages used at the external skin location are chosen based on the size and position of the wound and the relative position and proximity of the bone from which the ultrasonic waves are reflected. Thus, more than one ultrasound bandage or ultrasound transducer array bandage can be employed at the site of the wound. For example, bandages 10 can be employed about a wound 50 on a body 52 and positioned and configured to provide enhanced healing treatment to wound 50 as generally depicted in FIG. 9 and FIG. 10. A portable MOU is shown for providing power and control to transducers 16 via connectors 26. Additionally, for example, ultrasound transducer array bandage 30 having a plurality of transducer materials 32 can be disposed over a wound 54 on a body 56 for treatment thereof with a portable MOU connected thereto.

Typically, the frequency of the acoustic energy applied during treatment will be in the range of from about 20 kHz to about 10 MHZ and preferably from about 0.5 to about 5 MHZ. Features characterizing the frequency of the acoustic energy are disclosed in U.S. Pat. No. 5,520,612, the contents of which are incorporated by reference herein. It is to be understood that multiple sections of the human anatomy can be treated with multiple ultrasound bandages or ultrasound transducer array bandages at the same time. Thus, for example, in the case of an individual suffering from both an abrasion to the arm and an abrasion to the leg, an ultrasound bandage or ultrasound transducer array bandage can be applied to the arm while a second ultrasound bandage or ultrasound transducer array bandage is being applied to the section of the leg suffering from the wound. The transmit frequency and acoustic energy applied to each section can vary according to the foregoing ranges.

When applying the foregoing bandages to the section of the human anatomy in need of therapeutic assistance, it is advantageous to apply a coupling gel to the transducer material prior to its employment on the part of the body. Additionally, when employing the foregoing ultrasound transducer array bandages, it may be desirable in certain cases to use selective energization of the transducer materials in the array such that certain elements will generate acoustic energy while other elements will not. This will permit the spatial, temporal, and frequency control of the distribution of acoustic energy in the body. Techniques for altering the acoustic energy of the transducer materials are disclosed in U.S. Pat. No. 5,520,612.

Although the present invention has been described in preferred forms with a certain degree of particularity, many changes and variations are possible therein and will be apparent to those skilled in the art after reading the foregoing description. It is therefore to be understood that the present invention may be practiced otherwise than as specifically described herein without departing from the spirit and scope thereof.

What is claimed is:

1. An ultrasound bandage which comprises:
   a) a backing layer possessing upper and lower surfaces;
   b) an adhesive layer applied to, and substantially coextensive with, the lower surface of the backing layer; and,
   c) a transducer material disposed on at least a portion of the adhesive layer, comprising a fiber sheet formed from a composition containing a piezoelectric material.

2. The ultrasound bandage of claim 1 wherein the backing layer is a polyurethane film.

3. The ultrasound bandage of claim 1 wherein the adhesive layer is fabricated from a material selected from the group consisting of polyacrylic resin, polyvinylether resin and polyurethane resin.

4. The ultrasound bandage of claim 1 wherein the fiber sheet is a fabric woven from one or more fibers containing a piezoelectric material.

5. The ultrasound bandage of claim 1 wherein the piezoelectric material is selected from the group consisting of PZT powders, ceramic, PVDF, lead zirconate titanate $Pb(Zr,Ti)O_3$, lead metaniobate $Pb(Nb_2O_6)$ modified lead titanate $PbTi_3$, $(Pb,Ca)TiO_3$, $(Pb,Sm)TiO_3$, barium titanate $BaTiO_3$, PMN—PT$(1-x)Pb(Mg_{1/3},Nb_{2/3})O_3$-$xPbTiO_3$, PZN—PT/BT $Pb(Zn_{1/3},Nb_{2/3})O_3$-$xPbTiO_3$—$BaTiO_3$, $(1-x)Pb(Zn_{1/3},Nb_{2/3})O_3$-$x(yPbTiO_3$—$(1-y)PbZrO_3)$ and mixtures thereof.

6. The ultrasound bandage of claim 1 wherein the fiber sheet is knitted, braided or woven from extruded fibers containing a piezoelectric material.

7. The ultrasound bandage of claim 1 wherein the extruded fibers possess a coating formed thereon.

8. The ultrasound bandage of claim 7 wherein the coating comprises a film-forming polymer solution.

9. The ultrasound bandage of claim 8 wherein the film-forming polymer solution contains a mixture of a polyvinyl alcohol and polyvinyl acetate as a major component thereof and polyethylene glycol as a minor component thereof.

10. The ultrasound bandage of claim 1 further comprising an electrode surface applied to, and substantially coextensive with, opposite surfaces of the transducer material and a matching layer applied to, and substantially coextensive with, one of the electrode surfaces.

11. The ultrasound bandage of claim 10 further comprising a coupling pad applied to, and substantially coextensive with, the matching layer.

12. The ultrasound bandage of claim 11 wherein the coupling pad is a hydrogel pad.

13. The ultrasound bandage of claim 11 wherein the coupling pad is configured as a wedge to direct a longitudinal wave from the transducer material off-axis for to an internal designated reflection site and/or for modal conversion.

14. The ultrasound bandage of claim 13 further comprising a cover covering the adhesive layer and the coupling pad and being applied to the adhesive layer.

15. The ultrasound bandage of claim 10 wherein the matching layer comprises a polymeric material and optionally a filler.

16. The ultrasound bandage of claim 15 wherein the polymeric material is selected from the group consisting of thermoplastics, thermosets, rubbers, epoxy and mixtures thereof.

17. The ultrasound bandage of claim 15 wherein the matching layer includes a filler selected from the group consisting of PZT, tungsten, alumina, silica glass, tungsten carbide and titanium.

18. The ultrasound bandage of claim 15 wherein the matching layer includes glass powder as a filler.

19. The ultrasound bandage of claim 10 wherein the matching layer has an acoustic impedance of from about 2.0 to about 7.0 MRayls.

20. The ultrasound bandage of claim 1 further comprising connector assemblies having connectors and leads, the connectors detachably connect leads to the transducer material and the leads are coupled to a portable main operating unit.

21. A method for manufacturing an ultrasound bandage which comprises:
   a) providing a backing layer possessing upper and lower surfaces;
   b) applying an adhesive layer to, and substantially coextensive with, the lower surface of the backing layer; and,
   c) disposing a transducer material on at least a portion of the adhesive layer, comprising a fiber sheet formed from a composition containing a piezoelectric material.

22. The method of claim 21 wherein the backing layer is a polyurethane film.

23. The method of claim 21 wherein the adhesive layer is fabricated from a material selected from the group consisting of polyacrylic resin, polyvinylether resin and polyurethane resin.

24. The method of claim 21 wherein the fiber sheet is a fabric woven from one or more fibers containing a piezoelectric material.

25. The method of claim 21 wherein the piezoelectric material is selected from the group consisting of PZT powders, ceramic, PVDF, lead zirconate titanate $Pb(Zr,Ti)O_3$, lead metaniobate $Pb(Nb_2O_6)$ modified lead titanate $PbTi_3$, $(Pb,Ca)TiO_3$, $(Pb,Sm)TiO_3$, barium titanate $BaTiO_3$, PMN—PT$(1-x)Pb(Mg_{1/3},Nb_{2/3})O_3$-$xPbTiO_3$, PZN—PT/BT $Pb(Zn_{1/3},Nb_{2/3})O_3$-$xPbTiO_3$—$BaTiO_3$, $(1-x)Pb(Zn_{1/3},Nb_{2/3})O_3$-$x(yPbTiO_3$-$(1-y)PbZrO_3)$ and mixtures thereof.

26. The method of claim 21 wherein the extruded fibers possess a coating formed thereon.

27. The method of claim 26 wherein the coating comprises a film-forming polymer solution.

28. The method of claim 27 wherein the film-forming polymer solution contains a mixture of a polyvinyl alcohol and polyvinyl acetate as a major component thereof and polyethylene glycol as a minor component thereof.

29. The method of claim 21 further comprising an electrode surface applied to, and substantially coextensive with, opposite surfaces of the transducer material and a matching layer applied to, and substantially coextensive with, one of the electrode surfaces.

30. The method of claim 29 wherein the matching layer comprises a polymeric material and optionally a filler.

31. The method of claim 30 wherein the polymeric material is selected from the group consisting of thermoplastics, thermosets, rubbers, epoxy and mixtures thereof.

32. The method of claim 30 wherein the matching layer includes, a filler selected from the group consisting of PZT, tungsten, alumina, silica glass, tungsten carbide and titanium.

33. The method of claim 30 wherein the matching layer includes glass powder as a filler.

34. The method of claim 29 wherein the matching layer has an acoustic impedance of from about 2.0 to about 7.0 MRayls.

35. The method of claim 29 further comprising applying a coupling pad to, and substantially coextensive with, the matching layer.

36. The method of claim 35 wherein the coupling pad is a hydrogel pad.

37. The method of claim 35 wherein the coupling pad is configured as a wedge to direct a longitudinal wave from the transducer material off-axis for to an internal designated reflection site and/or for modal conversion.

38. The method of claim 21 further comprising connecting connector assemblies having connectors and leads to the transducer material of the ultrasonic bandage.

39. An ultrasound transducer array bandage which comprises:
   a) a backing layer possessing upper and lower surfaces;
   b) an adhesive layer applied to, and substantially coextensive with, the lower surface of the backing layer;
   c) an array comprising a plurality of transducer materials arranged in adjacent relation to define spaces there between, the array being disposed on at least a portion of the adhesive layer; and,
   d) a connector assembly applied to the array;
wherein each transducer material comprises a fiber sheet formed from a composition containing a piezoelectric material.

40. The ultrasound transducer array bandage of claim 39 wherein the backing layer is a polyurethane film.

41. The ultrasound transducer array bandage of claim 39 wherein the adhesive layer is fabricated from a material selected from the group consisting of polyacrylic resin, polyvinylether resin and polyurethane resin.

42. The ultrasound transducer array bandage of claim 39 wherein the fiber sheet is a fabric woven from one or more extruded fibers containing a piezoelectric material.

43. The ultrasound transducer array bandage of claim 39 wherein the piezoelectric material is selected from the group consisting of PZT powders, ceramic, PVDF, lead zirconate titanate $Pb(Zr,Ti)O_3$, lead metaniobate $Pb(Nb_2O_6)$ modified lead titanate $PbTi_3$, $(Pb,Ca)TiO_3$, $(Pb,Sm)TiO_3$, barium titanate $BaTiO_3$, PMN—PT$(1-x)Pb(Mg_{1/3},Nb_{2/3})O_3$-$xPbTiO_3$, PZN—PT/BT $Pb(Zn_{1/3},Nb_{2/3})O_3$-$xPbTiO_3$—$BaTiO_3$, $(1-x)Pb(Zn_{1/3},Nb_{2/3})O_3x(yPbTiO_3$-$(1-y)PbZrO_3)$ and mixtures thereof.

44. The ultrasound transducer array bandage of claim 39 wherein the fiber sheet is knitted, braided or woven from extruded fibers containing a piezoelectric material.

45. The ultrasound transducer array bandage of claim 39 wherein the extruded fibers possess a coating formed thereon.

46. The ultrasound transducer array bandage of claim 45 wherein the coating comprises a film-forming polymer solution.

47. The ultrasound transducer array bandage of claim 46 wherein the film-forming polymer solution contains a mixture of a polyvinyl alcohol and polyvinyl acetate as a major component thereof and polyethylene glycol as a minor component thereof.

48. The ultrasound transducer array bandage of claim 39 further comprising an electrode surface applied to, and substantially coextensive with, opposite surfaces of each transducer material and a matching layer applied to, and substantially coextensive with, one of the electrode surfaces.

49. The ultrasound transducer array bandage of claim 48 wherein the matching layer comprises a polymeric material and optionally a filler.

50. The ultrasound transducer array bandage of claim 49 wherein the polymeric material is selected from the group consisting of thermoplastics, thermosets, rubbers, epoxy and mixtures thereof.

51. The ultrasound transducer array bandage of claim 49 wherein the matching layer includes a filler selected from the group consisting of PZT, tungsten, alumina, silica glass, tungsten carbide and titanium.

52. The ultrasound transducer array bandage of claim 49 wherein the matching layer includes glass powder as a filler.

53. The ultrasound bandage of claim 48 wherein the matching layer has an acoustic impedance of from about 2.0 to about 7.0 MRayls.

54. The ultrasound transducer array bandage of claim 48 further comprising a coupling pad applied to, and substantially coextensive with, the matching layer.

55. The ultrasound transducer array bandage of claim 54 wherein the coupling pad is a hydrogel pad.

56. The ultrasound transducer array bandage of claim 54 wherein the coupling pad is configured as a wedge to direct a longitudinal wave from each transducer material off-axis for to an internal designated reflection site and/or for modal conversion.

57. The ultrasound transducer array bandage of claim 39 wherein the connector assemblies comprise connectors and leads, the connectors detachably connect leads to the array and the leads are coupled to a portable main operating unit.

58. The ultrasound transducer array bandage of claim 39 further comprising a cover covering the adhesive layer and the coupling pad and being applied to the adhesive layer.

59. A method for manufacturing an ultrasound transducer array bandage which comprises:
   a) providing a backing layer possessing upper and lower surfaces;
   b) applying an adhesive layer to, and substantially coextensive with, the lower surface of the backing layer;
   c) disposing an array comprising a plurality of transducer materials arranged in adjacent relation to define spaces there between on at least a portion of the adhesive layer; and,
   d) applying a connector assembly to the array;
wherein each transducer material comprises a fiber sheet formed from a composition containing a piezoelectric material.

60. The method of claim 59 wherein the backing layer is a polyurethane film.

61. The method of claim 59 wherein the adhesive layer is fabricated from a material selected from the group consisting of polyacrylic resin, polyvinylether resin and polyurethane resin.

62. The method of claim 59 wherein the piezoelectric material is selected from the group consisting of PZT powders, ceramic, PVDF, lead zirconate titanate Pb(Zr,Ti)$O_3$, lead metaniobate Pb(Nb$_2$O$_6$) modified lead titanate PbTi$_3$, (Pb,Ca)TiO$_3$, (Pb,Sm)TiO$_3$, barium titanate BaTiO$_3$, PMN—PT(1-x)Pb(Mg$_{1/3}$,Nb$_{2/3}$)O$_3$-xPbTiO$_3$, PZN—PT/BT Pb(Zn$_{1/3}$,Nb$_{2/3}$)O$_3$-xPbTiO$_3$—BaTiO$_3$, (1-x)Pb(Zn$_{1/3}$, Nb$_{2/3}$)O$_3$-x(yPbTiO$_3$-(1-y)PbZrO$_3$) and mixtures thereof.

63. The method of claim 59 wherein the fiber sheet is a fabric woven from one or more fibers containing a piezoelectric material.

64. The method of claim 59 further comprising the step of forming the fiber sheet by knitting, braiding or weaving the extruded fibers.

65. The method of claim 64 further comprising applying a coating to the extruded fibers prior to forming the fiber sheet.

66. The method of claim 65 wherein the coating comprises a film-forming polymer solution.

67. The method of claim 66 wherein the film-forming polymer solution contains a mixture of a polyvinyl alcohol and polyvinyl acetate as a major component thereof and polyethylene glycol as a minor component thereof.

68. The method of claim 59 further comprising an electrode surface applied to, and substantially coextensive with, opposite surfaces of each transducer material and a matching layer applied to, and substantially coextensive with, one of the electrode surfaces.

69. The method of claim 68 wherein the matching layer comprises a polymeric material and optionally a filler.

70. The method of claim 69 wherein the polymeric material is selected from the group consisting of thermoplastics, thermosets, rubbers, epoxy and mixtures thereof.

71. The method of claim 69 wherein the matching layer includes a filler selected from the group consisting of PZT, tungsten, alumina, silica glass, tungsten carbide and titanium.

72. The method of claim 69 wherein the matching layer includes glass powder as a filler.

73. The ultrasound bandage of claim 68 wherein the matching layer has an acoustic impedance of from about 2.0 to about 7.0 MRayls.

74. The method of claim 68 further comprising applying a coupling pad to, and substantially coextensive with, the matching layer.

75. The method of claim 74 wherein the coupling pad is a hydrogel pad.

76. The method of claim 74 wherein the coupling pad is configured as a wedge to direct a longitudinal wave from each transducer material off-axis for to an internal designated reflection site and/or for modal conversion.

77. The method of claim 59 wherein the connector assemblies comprise connectors and leads.

78. A method for accelerating the healing of wounds comprising:
   a) positioning at least one ultrasound bandage adjacent to a body at the site of a wound;
   b) the ultrasound bandage comprising:
      i) a backing layer possessing upper and lower surfaces;
      ii) an adhesive layer applied to, and substantially coextensive with, the lower surface of the backing layer; and,
      iii) a transducer material disposed on at least a portion of the adhesive layer,
   wherein the transducer material comprises a fiber sheet formed from a composition containing a piezoelectric material; and,
   c) causing the transducer material to generate ultrasonic pulses.

79. The method of claim 78 wherein at least one ultrasound bandage is positioned adjacent to a body at a plurality of sites of wounds.

80. The method of claim 78 further comprising applying an electrode surface to, and substantially coextensive with, opposite surfaces of the transducer material, applying a matching layer to, and substantially coextensive with, one of the electrode surfaces and applying a coupling pad configured as a wedge to the matching layer.

81. A method for accelerating the healing of wounds comprising:
   a) positioning at least one ultrasound transducer array bandage adjacent to a body at the site of a wound;
   b) the ultrasound transducer array bandage comprising:
      i) a backing layer possessing upper and lower surfaces;
      ii) an adhesive layer applied to, and substantially coextensive with, the lower surface of the backing layer; and,
      iii) an array comprising a plurality of transducer materials arranged in adjacent relation to define spaces there between, the array being disposed on at least a portion of the adhesive layer, wherein the transducer material comprises a fiber sheet formed from a composition containing a piezoelectric material, and,
   c) causing the plurality of transducer materials to generate ultrasonic pulses.

82. The method of claim 81 wherein at least one ultrasound transducer array bandage is positioned adjacent to a body at a plurality of sites of wounds.

83. The method of claim 81 further comprising applying an electrode surface to, and substantially coextensive with, opposite surfaces of each transducer material, applying a matching layer to, and substantially coextensive with, one of the electrode surfaces and applying a coupling pad configured as a wedge to the matching layer.

* * * * *